United States Patent [19]
Arai et al.

[11] Patent Number: 4,888,042
[45] Date of Patent: Dec. 19, 1989

[54] CYCLOHEXENONE DERIVATIVE, PROCESS FOR PRODUCING THE SAME AND HERBICIDES COMPRISING THE SAME AS ACTIVE INGREDIENT

[75] Inventors: Kenji Arai, Toyonaka; Kouichi Morita, Kasai; Nobuaki Mito, Takarazuka; Naonori Hirata, Sakai, all of Japan

[73] Assignee: Sumitomo Chemical Company, Limited, Osaka, Japan

[21] Appl. No.: 208,600

[22] Filed: Jun. 20, 1988

[30] Foreign Application Priority Data

Jul. 3, 1987 [JP] Japan ................................ 62-167639

[51] Int. Cl.[4] ........................................ A01N 43/00

[52] U.S. Cl. ........................................ 71/88; 71/91; 71/94; 71/98; 71/100; 564/256; 560/124; 560/9; 560/107; 560/27; 560/163; 562/426; 549/420; 549/28

[58] Field of Search ........................ 71/98, 100, 88, 91, 71/94; 564/256; 560/124, 9, 107, 27, 103; 562/426; 549/420, 28; 260/455 A; 546/318; 558/175

[56] References Cited

U.S. PATENT DOCUMENTS

| | | | |
|---|---|---|---|
| 4,249,937 | 2/1981 | Iwataki et al. | 564/256 |
| 4,515,729 | 5/1985 | Iwataki et al. | 71/98 |
| 4,555,263 | 11/1985 | Serban et al. | 71/98 |
| 4,652,303 | 3/1987 | Watson et al. | 71/98 |
| 4,717,418 | 1/1988 | Warna et al. | 71/98 |
| 4,728,357 | 3/1988 | Becker et al. | 71/98 |
| 4,741,768 | 5/1988 | Frazier et al. | 71/98 |
| 4,746,350 | 5/1988 | Watson | 71/98 |

*Primary Examiner*—James H. Reamer
*Attorney, Agent, or Firm*—Stevens, Davis, Miller & Mosher

[57] ABSTRACT

The present compounds have a high herbicidal activity against various problematic weeds in soil treatment and foliage treatment in plow field as well as in treatment under flooded condition in paddy field, and besides they exhibit a high selectivity to the weeds from the main crops, so that they can be used in various applications as an active ingredient for herbicides.

11 Claims, No Drawings

CYCLOHEXENONE DERIVATIVE, PROCESS FOR PRODUCING THE SAME AND HERBICIDES COMPRISING THE SAME AS ACTIVE INGREDIENT

The present invention relates to a novel cyclohexenone derivative, a process for producing the same and herbicides comprising the same as an active ingredient.

JP-A-54-46749 and JP-A-54-115349 disclose a certain kind of cyclohexane derivatives can be used as an active ingredient for herbicides.

These compounds, however, are unsatisfactory because of their poor herbicidal activity and poor selectivity to weeds from crops.

In recognition of the situation, the present inventors have extensively studied to develop a compound having a high herbicidal activity. As a result, they have found a compound having a high herbicidal activity at low dosage rates and exhibiting no problematic phytotoxicity to crops. The present invention is based on the finding.

According to the present invention, there are provided a cyclohexenone derivative represented by the formula (I) (hereinafter referred to as the present compound),

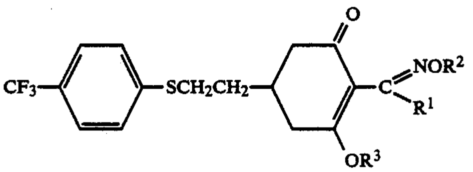
(I)

wherein $R^1$ represents a $(C_1-C_3)$alkyl group, $R^2$ represents a $(C_1-C_3)$alkyl, $(C_3-C_4)$alkenyl, propargyl or chloroallyl group, and $R^3$ represents a $(C_1-C_{12})$alkyl, $(C_3-C_5)$alkenyl, propargyl, halo$(C_2-C_3)$alkyl, halo$(C_3-C_4)$alkenyl, $(C_3-C_6)$cycloalkyl, $(C_5-C_7)$cycloalkenyl, $(C_1-C_8)$alkoxy$(C_1-C_2)$alkyl, methylthiomethyl, halo$(C_2-C_4)$alkoxymethyl, benzyloxymethyl (which may be substituted with a $(C_1-C_2)$alkyl group or halogen atom), carboxy$(C_1-C_4)$alkyl, $(C_1-C_5)$alkoxycarbonyl$(C_1-C_4)$alkyl, di$(C_1-C_3)$alkylcarbamoyl, di$(C_1-C_3)$alkylthiocarbamoyl, O,O-di$(C_1-C_3)$alkoxyphosphinyl, $(C_1-C_{11})$alkylcarbonyl, $(C_2-C_4)$alkenylcarbonyl, $(C_3-C_6)$cycloalkylcarbonyl, $(C_3-C_6)$cycloalkylacetyl, chrysanthemoyl, benzoyl (which may be substituted with a $(C_1-C_2)$alkyl group or halogen atom), naphthalenecarbonyl, pyridinecarbonyl, furoyl or thenoyl (which may be substituted with a $(C_1-C_2)$alkyl group or halogen atom);

a process for producing the same and herbicides comprising the same as an active ingredient.

A method for producing the present compounds is explained below.

Among the present compounds (I), preferred are those wherein $R^1$ is methyl and $R^2$ is ethyl.

And more preferred are those wherein $R^1$ is methyl, $R^2$ is ethyl and $R^3$ is methyl, propargyl, $(C_1-C_5)$alkoxymethyl, halo$(C_2-C_4)$alkoxymethyl, methylthiomethyl, carboxymethyl, 1-carboxyethyl, $(C_1-C_{11})$alkylcarbonyl, thenoyl, etc.

Typical examples of the preferred compounds are those wherein $R^1$ is methyl, $R^2$ is ethyl and $R^3$ is acetyl, isobutyryl, propoxymethyl, carboxymethyl, etc.

The present compounds can be produced by reacting a compound represented by the formula (II),

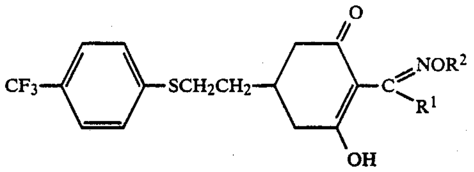
(II)

wherein $R^1$ and $R^2$ represent the same meanings as described above, with a compound represented by the formula (III), $R^3$—X (III)

wherein $R^3$ represents the same meaning as defined above, and X represents a halogen.

This reaction is usually carried out with or without a solvent in the presence of a dehydrohalogenating agent. The range of the reaction temperature is from 0° to 100° C., and that of the reaction time is from several minutes to several hours. The amount used of the compound represented by the formula (III) ranges from 1 to 5 equivalents based on 1 equivalent of the compound represented by the formula (II). And the amount used of the dehydrohalogenating agent ranges from 1 to 2 equivalents based on the same.

The solvent includes aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. acetone, methyl ethyl ketone, methyl isobutyl ketone, isophorone, cyclohexanone), alcohols (e.g. methanol, ethanol, isopropanol, tert-butanol, octanol, cyclohexanol, methyl cellosolve, diethylene glycol, glycerin), esters (e.g. ethyl acetate, butyl acetate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethyl sulfoxide, sulfolane), water and mixtures thereof.

The dehydrohalogenating agent includes organic bases (e.g. pyridine, triethylamine, N,N-diethylaniline), inorganic bases (e.g. sodium hydroxide, potassium hydroxide, sodium carbonate, potassium carbonate, sodium hydride), alkali metal alkoxides (e.g. sodium methoxide, sodium ethoxide), etc.

After the reaction has been completed, the reaction solution is treated as usual, that is, poured into water, acidified if necessary, extracted with an organic solvent and concentrated. Thus, the desired present compound can be obtained. The product may be purified if necessary by operations such as chromatography, distillation, recrystallization, etc.

The following Table 1 shows some of the present compounds produced by the method described above.

TABLE 1

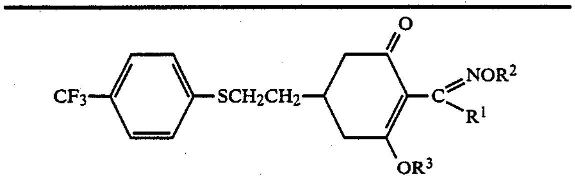

| $R^1$ | $R^2$ | $R^3$ |
|---|---|---|
| $CH_3$ | $C_2H_5$ | $CH_3$ |
| " | " | $C_2H_5$ |
| " | " | n-$C_4H_9$ |
| " | " | $(CH_2)_{11}CH_3$ |
| " | " | $CH(CH_3)_2$ |
| " | " | $CH_2CH{=}CH_2$ |
| " | " | $CH_2CH_2CH{=}CH_2$ |
| " | " | $CH_2CH{=}CHCH_3$ |
| " | " | $CH_2C{\equiv}CH$ |
| " | " | $CH_2CH_2Cl$ |
| " | " | $CH_2CH_2CH_2Cl$ |
| " | " | $CH_2CH{=}CHCl$ |
| " | " | 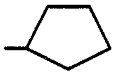 |
| " | " | 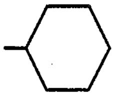 |
| " | " | 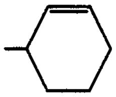 |
| " | " | $CH_2OCH_2CH_2CH_2CH_3$ |
| " | " | $CH_2O(CH_2)_4CH_3$ |
| $CH_3$ | $C_2H_5$ | $CH_2CH_2OC_2H_5$ |
| " | " | $CH_2SCH_3$ |
| " | " | $CH_2OCH_2CH_2F$ |
| " | " | $COCH_3$ |
| " | " | $COC_2H_5$ |
| " | " | $COCH(CH_3)_2$ |
| " | " | $COC(CH_3)_3$ |
| " | " | $COCH_2CH{=}CH_2$ |
| " | " | 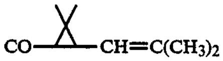 |
| " | " | $CH_2COOH$ |
| " | " | $CH_2COOCH_3$ |
| " | " | $CH(CH_3)COOC_2H_5$ |
| " | " | 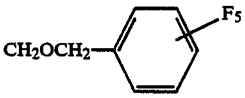 |
| " | " | $COC_6H_5$ |
| " | " | 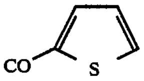 |
| " | " | 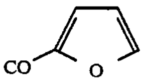 |
| " | " | 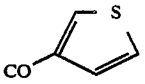 |

TABLE 1-continued

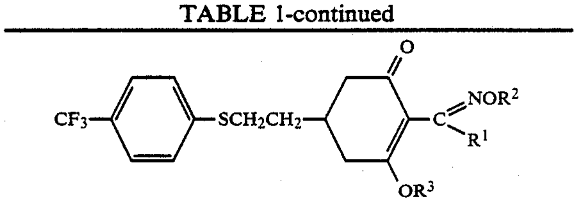

| $R^1$ | $R^2$ | $R^3$ |
|---|---|---|
| " | " | $CON(CH_3)_2$ |
| " | " | $CSN(CH_3)_2$ |
| $CH_3$ | $C_2H_5$ | $P(O)(OC_2H_5)_2$ |
| $C_2H_5$ | " | $CH_3$ |
| " | " | $C_2H_5$ |
| " | " | $CH(CH_3)_2$ |
| " | " | $CH_2CH{=}CH_2$ |
| " | " | $CH_2OCH_2CH_2CH_3$ |
| " | " | $COCH_3$ |
| " | " | $COCH_2CH_2CH_3$ |
| " | " | 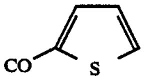 |
| " | " | 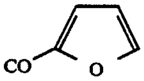 |
| " | " | $CH_2COOCH_3$ |
| " | " | 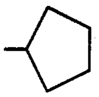 |
| n-$C_3H_7$ | " | $CH_3$ |
| " | " | 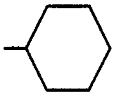 |
| " | " | $COCH_3$ |
| " | " | 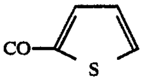 |
| " | " | $CH_2O(CH_2)_3CH_3$ |
| n-$C_3H_7$ | $C_2H_5$ | $CH_2CH_2Cl$ |
| " | " | $CH_2CH_2OC_2H_5$ |
| " | " | $CH_2C{\equiv}CH$ |
| " | " | $CH_2CH{=}CHCl$ |
| $CH_3$ | n-$C_3H_7$ | $CH_3$ |
| " | " | $CH(CH_3)_2$ |
| " | " | $COCH_3$ |
| " | " | 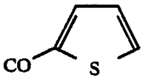 |
| " | " | $CH_2CH{=}CH_2$ |
| " | " | $CH_2CH{=}CHCH_3$ |
| " | " | $(CH_2)_3Cl$ |
| " | " | $CH_2OCH_2CH_2CH_3$ |
| $C_2H_5$ | " | $CH_3$ |
| " | " | $C(CH_3)_3$ |
| " | " | $COCH_3$ |
| " | " | 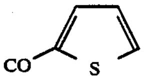 |

TABLE 1-continued

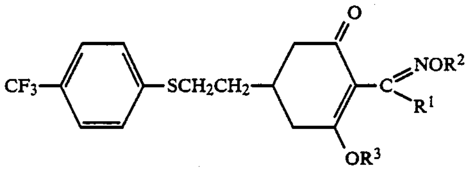

| $R^1$ | $R^2$ | $R^3$ |
|---|---|---|
| " | " | $COC_6H_5$ |
| " | " | $CH_2C\equiv CH$ |
| " | " | $CH_2CH{=}CH_2$ |
| " | " | $CH_2OCH_2CH_2CH_3$ |
| " | " | $CH_2SCH_3$ |
| n-$C_3H_7$ | " | $CH_3$ |
| n-$C_3H_7$ | n-$C_3H_7$ | $COCH_3$ |
| " | " | 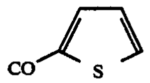 |
| " | " | $CH_2CH_2CH{=}CH_2$ |
| " | " | $CH_2COOCH_3$ |
| $CH_3$ | $CH_2CH{=}CH_2$ | $CH_3$ |
| " | " | $C_2H_5$ |
| " | " | 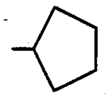 |
| " | " | $COCH_3$ |
| " | " | 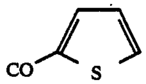 |
| " | " | $CH_2CH{=}CH_2$ |
| " | " | $CH_2CH{=}CHCH_3$ |
| " | " | $CH_2C\equiv CH$ |
| " | " | $CH_2OCH_2CH_2CH_3$ |
| " | " | $CH_2SCH_3$ |
| " | " | $CH_2CH_2Cl$ |
| " | " | $CH_2COOH$ |
| $C_2H_5$ | " | $CH_3$ |
| " | " | $COCH_3$ |
| " | " | $CH_2C\equiv CH$ |
| " | " | $CH_2O(CH_2)_4CH_3$ |
| $C_2H_5$ | $CH_2CH{=}CH_2$ | $CH_2CH{=}CHCl$ |
| n-$C_3H_7$ | " | $CH_3$ |
| " | " | $COCH_3$ |
| " | " | 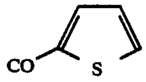 |
| " | " | $CH_2CH{=}CHCH_3$ |
| " | " | $CH_2OCH_2CH_2CH_3$ |
| $CH_3$ | $CH_2CH{=}CHCl$ | $CH_3$ |
| " | " | $C_2H_5$ |
| " | " | $CH_2CH_2Cl$ |
| " | " | 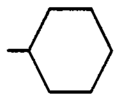 |
| " | " | $CH_2CH{=}CH_2$ |
| " | " | $CON(CH_3)_2$ |
| " | " | $CH_2CH_2CH{=}CH_2$ |
| " | " | $CH_2C\equiv CH$ |
| " | " | $CH_2O(CH_2)_3CH_3$ |
| " | " | $COCH_3$ |

TABLE 1-continued

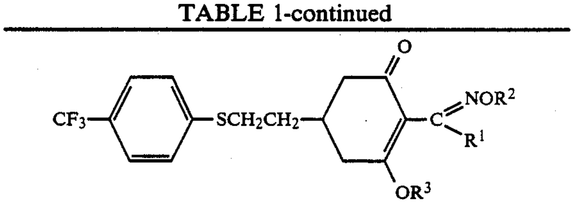

| $R^1$ | $R^2$ | $R^3$ |
|---|---|---|
| " | " | 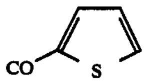 |
| " | " | $COC_6H_5$ |
| $C_2H_5$ | " | $CH_3$ |
| " | " | $COCH_3$ |
| $C_2H_5$ | $CH_2CH{=}CHCl$ | 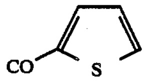 |
| " | " | $CH_2CH{=}CH_2$ |
| " | " | $CH_2OCH_2CH_2CH_3$ |
| " | " | $CH_2SCH_3$ |
| " | " | $CH_2COOCH_3$ |
| n-$C_3H_7$ | " | $CH_3$ |
| " | " | $COCH_3$ |
| " | " | 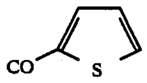 |
| " | " | $CH_2CH{=}CH_2$ |
| $CH_3$ | $CH_2CH{=}CHCH_3$ | $CH_3$ |
| " | " | $COCH_3$ |
| " | " | 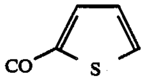 |
| " | " | $CH_2CH{=}CH_2$ |
| " | " | 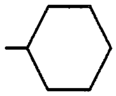 |
| " | " | $CH_2C\equiv CH$ |
| " | " | $CH_2OCH_2CH_2CH_3$ |
| " | " | $CH_2SCH_3$ |
| " | " | $CON(CH_3)_2$ |
| " | " | $CH_2COOH$ |
| $C_2H_5$ | $CH_2CH{=}CHCH_3$ | $CH_3$ |
| " | " | $COCH_3$ |
| " | " | $CH_2OCH_2CH_2CH_3$ |
| " | " | 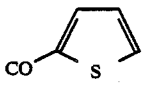 |
| " | " | $CH_2CH{=}CH_2$ |
| " | " | $CH_2C\equiv CH$ |
| n-$C_3H_7$ | " | $CH_3$ |
| " | " | $COCH_3$ |
| " | " | 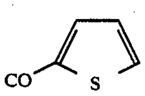 |
| " | " | $CH_2OCH_2CH_2CH_3$ |
| " | " | $CH_2CH{=}CH_2$ |
| " | " | $CH_2COOH$ |

TABLE 1-continued

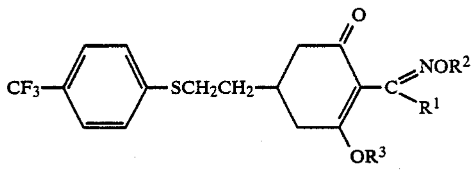

| $R^1$ | $R^2$ | $R^3$ |
|---|---|---|
| $CH_3$ | $CH_2C \equiv CH$ | $CH_3$ |
| " | " | $COCH_3$ |
| " | " | $CH_2CH=CH_2$ |
| " | " | $CH_2C \equiv CH$ |
| " | " | 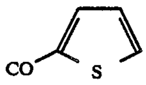 |
| " | " | 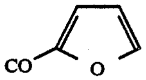 |
| " | " | $CH_2O(CH_2)_4CH_3$ |
| $C_2H_5$ | $CH_2C \equiv CH$ | $CH_3$ |
| " | " | $COCH_3$ |
| " | " | $CH_2OCH_2CH_2CH_3$ |
| " | " | $CH_2C \equiv CH$ |
| n-$C_3H_7$ | " | $CH_3$ |
| " | " | $COCH_3$ |
| " | " | $CH_2OCH_2CH_2CH_3$ |
| " | " | $CH_2CH=CH_2$ |
| $CH_3$ | $CH_3$ | $COC_3H_7$—n |
| " | " | $CH_2OC_2H_5$ |
| " | $CH_2CH_2CH=CH_2$ | $COCH_3$ |
| " | " | 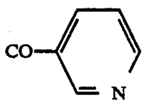 |
| " | $C_2H_5$ | $-CH-CH=CHCl$<br>$CH_3$ |
| " | " | 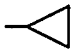 |
| " | " | 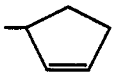 |
| " | " | 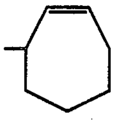 |
| " | " | $CH_2OCH_3$ |
| " | " | $CH_2OC_8H_{17}$—n |
| " | " | $CH_2O(CH_2)_4Cl$ |
| $CH_3$ | $C_2H_5$ | $CH_2O(CH_2)_3Br$ |
| " | " | 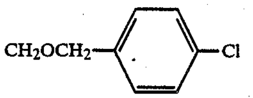 |

TABLE 1-continued

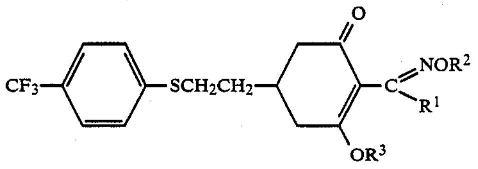

| $R^1$ | $R^2$ | $R^3$ |
|---|---|---|
| " | " | 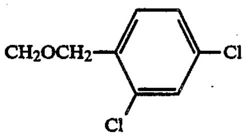 |
| " | " | 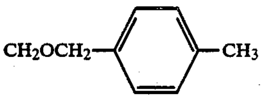 |
| " | " | $-CHCO_2H$<br>$CH_3$ |
| " | " | $-CHCH_2CO_2H$<br>$CH_3$ |
| " | " | $-CHCH_2CO_2C_5H_{11}$—n<br>$CH_3$ |
| " | " | $-(CH_2)_4CO_2C_4H_9$—n |
| " | " | $CON(C_2H_5)_2$ |
| " | " | $CSN(C_2H_5)_2$ |
| " | " | $CON(C_3H_7$—n$)_2$ |
| " | " | $CSN(C_3H_7$—n$)_2$ |
| " | " | $P(O)(OCH_3)_2$ |
| $C_2H_5$ | " | $P(O)(OC_3H_7$—n$)_2$ |
| $CH_3$ | $C_2H_5$ | 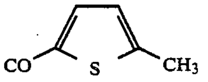 |
| " | " | 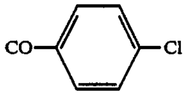 |
| " | " | 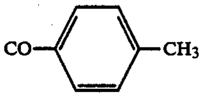 |
| $CH_3$ | $C_2H_5$ | 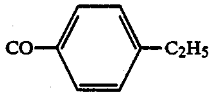 |
| " | " | 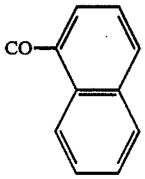 |
| " | " | $COCH=CH_2$ |
| " | " | $COCH=C(CH_3)_2$ |

TABLE 1-continued

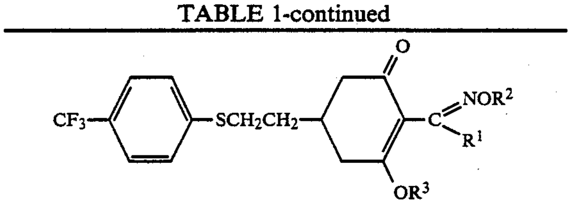

| $R^1$ | $R^2$ | $R^3$ |
|---|---|---|
| " | " | 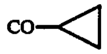 |
| " | " | 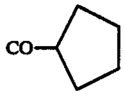 |
| " | " | 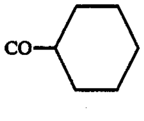 |
| " | " | 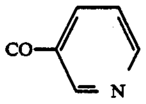 |
| " | " | 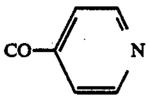 |

The compound represented by the formula (II), one of the materials for producing the present compounds, can be produced by the methods disclosed in EP-253537-A.

The present compounds, in foliage treatment and soil treatment in plow field, have a herbicidal activity against various undesired weeds. The specific examples of the weeds are broadleaf weeds such as common purslane (*Portulaca oleracea*), chickweed (*Stellaria media*), common lambsquarters (*Chenopodium album*), redroot pigweed (*Amaranthus retroflexus*), radish (*Raphanus sativus*), velvetleaf (*Abutilon theophrasti*), prickly sida (*Sida spinosa*), tall morningglory (*Ipomoea purpurea*), black nightshade (*Solanum nigrum*), birdseye speedwell (*Veronica persica*), etc.; Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oat (*Avena sativa*), wild oat (*Avena fatua*), johnsongrass (*Sorghum halepense*), quackgrass (*Agropyron repens*), downy brome (*Bromus tectorum*), cheat (*Bromus secalinus*), bermudagrass (*Cynodon dactylon*), giant foxtail (*Setaria faberi*), goosegrass (*Eleusine indica*), fall panicum (*Panicum dichotomiflorum*), shattercane (*Sorghum bicolor*), etc. Besides, the present compounds exhibit no problematic phytotoxicity to broadleaf crops (e.g. soybean, cotton, beet, peanut, sunflower). And surprisingly they exhibit selectivity between gramineous crops (e.g. corn, wheat, barley, rice) and troubling weeds. Especially they exhibit good selectivity between corn and troubling weeds.

Further, the present compounds, in treatment under flooded condition in paddy field, have a herbicidal activity against various undesired weeds. Specific examples of the weeds are grassy weeds such as barnyardgrass (*Echinochloa oryzicola*), etc., and broadleaf weeds such as common falsepimpernel (*Lindernia procumbens*), long stemmed waterwort (*Elatine triandra*), etc., and yet they exhibit no problematic phytotoxicity to rice.

Further, the present compounds can be used as a herbicide for paddy fields, plow fields, orchards, pastures, turfs, forests, non-crop lands, etc. Using the present compounds in mixture with other herbicides is expected to multiply their herbicidal activity. In addition, the present compounds can be used in mixture with insecticides, acaricides, nematocides, fungicides, plant growth regulators, fertilizers, soil improvers, etc.

When the present compounds are used as an active ingredient for herbicides, they are usually formulated into emulsifiable concentrates, wettable powders, suspension formulations, granules, etc. by mixing with solid carriers, liquid carriers, surface active agents and other auxiliaries for formulation.

These preparations contain the present compounds as an active ingredient in an amount of from 0.1 to 90% by weight, preferably from 0.2 to 80% by weight.

The solid carriers include fine powders or granules of kaolin clay, attapulgite clay, bentonite, terra abla, pyrophyllite, talc, diatomaceous earth, calcite, walnut shell powder, urea, ammonium sulfate, synthetic hydrated silicon oxide, etc. The liquid carriers include aromatic hydrocarbons (e.g. xylene, methylnaphthalene), alcohols (e.g. isopropanol, ethylene glycol, cellosolve), ketones (e.g. acetone, cyclohexanone, isophorone), vegetable oils (e.g. soybean oil, cotton seed oil), dimethyl sulfoxide, N,N-dimethylformamide, acetonitrile, water, etc.

The surface active agents used for emulsification, dispersion, wetting, etc. include anionic surface active agents such as the salt of alkyl sulfates, alkylsulfonates, alkylarylsulfonates, dialkyl sulfosuccinates, the salt of polyoxyethylene alkylaryl ether phosphoric acid esters, etc., and nonionic surface active agents such as polyoxyethylene alkyl ether, polyoxyethylene alkylaryl ether, polyoxyethylene polyoxypropylene block copolymers, sorbitan fatty acid esters, polyoxyethylene sorbitan fatty acid esters, etc.

Other auxiliaries for formulation include lignosulfonates, alginates, polyvinyl alcohol, gum arabic, CMC (carboxymethyl cellulose), PAP (isopropyl acid phosphate), etc.

The present compounds are usually formulated and used in soil treatment, foliage treatment or treatment under flooded conditions before or after the emergence of weeds. The soil treatment includes soil surface treatment, soil incorporation treatment, etc. The foliage treatment includes over-the-top-treatment for plants and directed treatment wherein herbicides are applied to weeds only with keeping crops from the exposure.

When the present compounds are used as an active ingredient for herbicides, their dosage rate may vary with weather conditions, preparation forms, when, how and where the treatments are applied, weeds and crops aimed at, etc. However it is usually from 0.05 to 200 g/are, preferably from 0.1 to 100 g/are. In the cases of emulsifiable concentrates, wettable powders, suspension formulations, etc., their prescribed amount is usually diluted with water of from 1 to 10 liters/are (if necessary, auxiliaries such as spreading agents are added). Granules, etc. are usually used as such without dilution.

The spreading agents include, in addition to the foregoing surface active agents, polyoxyethylene resin acids (esters), lignosulfonates, abietates, dinaphthylmethanedisulfonates, paraffin, etc.

The following production examples, formulation examples and test examples serve to give specific illustrations of the practice of the present invention but it is not intended in any way to limit the scope of the present invention.

PRODUCTION EXAMPLE 1

Production of the present compound (17)

To 10 ml of a dimethylformamide solution containing 0.04 g of suspended sodium hydride (60% oil suspension) was added 0.4 g of 2-(1-ethoxyaminoethylidene)-5-[2-(4-trifluoromethylphenylthio)ethyl]cyclohexane-1,3-dione. After stirring for 10 minutes, 0.20 g of allyl bromide was added to the resulting mixture which was then stirred overnight at room temperature. The reaction solution was poured into water, acidified and extracted with diethyl ether. The solvent was removed, and the residue obtained was treated by thin layer chromatography (developing solvent, hexane:ethyl acetate=2:1) to obtain 0.23 g of 1-allyloxy-2-(1-ethyloximinoethyl)-5-[2-(4-trifluoromethylphenylthio)ethyl]-1-cyclohexene-3-one.

$n_D^{21.5}$ 1.5259.

$^1$H-NMR spectrum ($CDCl_3$): δ(ppm) 7.37(4H, ABq), 6.2–5.6(1H, m), 5.34(1H, brd), 5.13(1H, m), 4.51(2H, d), 4.16(2H, q), 3.00(2H, t), 2.8–1.5(7H, m), 1.95(3H, s), 1.26(3H, t).

PRODUCTION EXAMPLE 2

Production of the present compound (19)

0.21 Gram of 2-(1-ethoxyaminopropylidene)-5-[2-(4-trifluoromethylphenylthio)ethyl]cyclohexane-1,3-dione was dissolved in 15 ml of diethyl ether. After adding 0.1 g of acetyl chloride and 0.07 g of triethylamine, the resulting mixture was stirred at room temperature for 3 hours. The reaction solution was poured into water and extracted with diethyl ether. The solvent was removed, and the residue obtained was treated by thin layer chromatography (developing solvent, hexane:ethyl acetate=3:1) to obtain 0.12 g of 1-acetoxy-2-(1-ethyloximinopropyl)-5-[2-(4-trifluoromethylphenylthio]ethyl-1-cyclohexene-3-one.

$n_D^{25}$ 1.5209.

$^1$H-NMR spectrum ($CDCl_3$): δ(ppm) 7.39(4H, ABq), 4.12(2H, q), 3.00(2H, t), 2.8–1.5(9H, m), 2.13(3H, s), 1.25(3H, t), 0.93(3H, t).

The following Table 2 shows some of the present compounds produced in the same manner as above.

TABLE 2

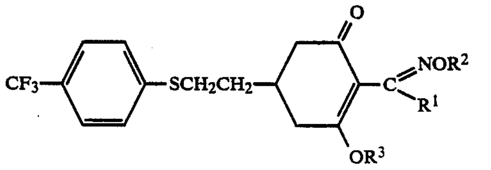

| Compound No. | $R^1$ | $R^2$ | $R^3$ | Refractive index (°C.) |
|---|---|---|---|---|
| (1) | $CH_3$ | $C_2H_5$ | $COCH_3$ | 1.5283 (22) |
| (2) | " | " | $CH(CH_3)COOC_2H_5$ | 1.5186 (23) |
| (3) | " | " | $CH_3$ | 1.5136 (22.5) |

TABLE 2-continued

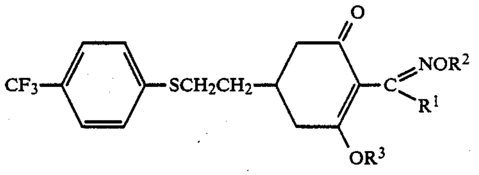

| Compound No. | $R^1$ | $R^2$ | $R^3$ | Refractive index (°C.) |
|---|---|---|---|---|
| (4) | " | " | 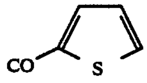 | 1.5436 (22.5) |
| (5) | " | " | $COC_6H_5$ | 1.5591 (22.5) |
| (6) | " | " | $CH_2COOCH_3$ | 1.5204 (24) |
| (7) | " | " | $P(O)(OC_2H_5)_2$ | 1.5048 (24) |
| (8) | " | " | $CH_2COOH$ | 1.5311 (24) |
| (9) | $C_2H_5$ | " | 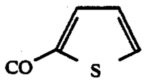 | 1.5481 (25) |
| (10) | $CH_3$ | " | 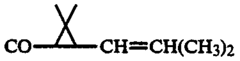 | 1.5216 (23) |
| (11) | " | " | $COCH(CH_3)_2$ | 1.5126 (23) |
| (12) | " | " | $COC(CH_3)_3$ | 1.5076 (23) |
| (13) | " | " | $CH_2OCH_2CH_2CH_3$ | 1.5252 (21.5) |
| (14) | " | " | $CH_2O(CH_2)_4CH_3$ | 1.5249 (21.5) |
| (15) | " | " | $CH_2OCH_2CH_2F$ | 1.5215 (21.5) |
| (16) | $CH_3$ | $C_2H_5$ | 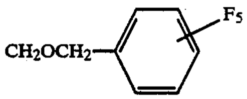 | 1.5220 (21.5) |
| (17) | " | " | $CH_2CH{=}CH_2$ | 1.5259 (21.5) |
| (18) | " | " | $CH_2C{\equiv}CH$ | 1.5405 (21.5) |
| (19) | $C_2H_5$ | " | $COCH_3$ | 1.5209 (25) |
| (20) | $CH_3$ | " | $CON(CH_3)_2$ | 1.5245 (21.5) |
| (21) | " | " | $CSN(CH_3)_2$ | 1.5492 (21.5) |
| (22) | " | " | $C_2H_5$ | 1.5355 (23) |
| (23) | " | " | n-$C_4H_9$ | 1.5230 (23) |
| (24) | " | " | $(CH_2)_{11}CH_3$ | 1.5116 (23) |
| (25) | " | " | $CH(CH_3)_2$ | 1.5275 (23) |
| (26) | " | " | 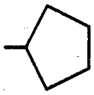 | 1.5309 (23) |
| (27) | " | " | 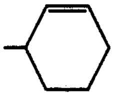 | 1.5411 (23) |
| (28) | " | " | $CH_2SCH_3$ | 1.5509 (25) |
| (29) | $C_2H_5$ | " | $CH_3$ | 1.5431 (25) |

The formulation examples are shown below. The present compounds are identified by Compound Nos. in Table 2. Parts in the examples are by weight.

FORMULATION EXAMPLE 1

Fifty parts of each of the present compounds (1) and (16), 3 parts of calcium lignosulfonate, 2 parts of sodium lauryl sulfate and 45 parts of synthetic hydrated silicon oxide are well pulverized and mixed to obtain a wettable powder.

FORMULATION EXAMPLE 2

Ten parts of each of the present compounds (1) through (29), 14 parts of polyoxyethylene styrylphenyl ether, 6 parts of calcium dodecylbenzenesulfonate, 30 parts of xylene and 40 parts of cyclohexanone are well mixed to obtain an emulsifiable concentrate of each compound.

and wet-pulverized until the particle size is reduced to 5 microns or less to obtain a suspension formulation.

The following test examples demonstrate the usefulness of the present compounds as an active ingredient for herbicides. In the test examples, the present compounds are identified by Compound Nos. in Table 2, and compounds used as a control are identified by Compound symbols in Table 3.

TABLE 3

| Compound symbol | Structural formula | Remark |
|---|---|---|
| A | 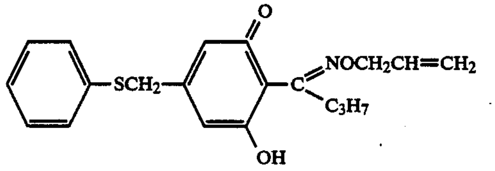 | Compound disclosed in JP-A-54-46749. |
| B | 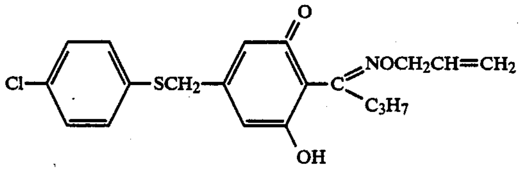 | Compound disclosed in JP-A-54-115349. |
| C | 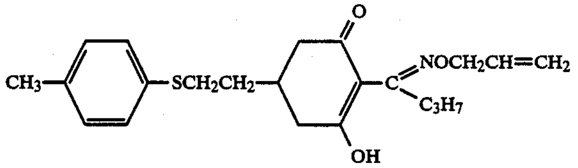 | Compound disclosed in JP-A-54-115349. |
| D | 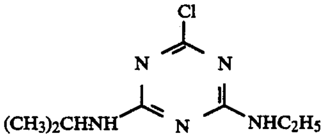 | Atrazine |
| E | 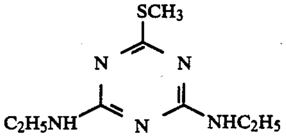 | Simetryn |

FORMULATION EXAMPLE 3

Two parts of each of the present compounds (3) and (4), 1 part of synthetic hydrated silicon oxide, 2 parts of calcium lignosulfonate, 30 parts of bentonite and 65 parts of kaolin clay are well pulverized and mixed, well kneaded with water, granulated and dried to obtain a granule of each compound.

FORMULATION EXAMPLE 4

Twenty-five parts of each of the present compounds (1) through (29), 3 parts of polyoxyethylene sorbitan monooleate, 3 parts of CMC and 69 parts of water are mixed and wet-pulverized until the particle size is reduced to 5 microns or less to obtain a suspension formulation of each compound.

FORMULATION EXAMPLE 5

Two parts of each of the present compounds (1) and (12), 1 part of polyethylene sorbitan monooleate, 5 parts of polyvinyl alcohol and 92 parts of water are mixed The herbicidal activity was evaluated in six grades, 0, 1, 2, 3, 4 and 5, according to the degrees of the emergence and growth inhibition of test plants macroscopically observed at the time of examination. The grade "0" means there being little or no difference in the degrees between the treated test plants and untreated ones; the grade "5" means the death or complete growth inhibition of the test plants; and the degrees between "0" and "5" were divided into four grades, 1, 2, 3 and 4.

TEST EXAMPLE 1

Foliage treatment test in plow field

Plow-field soil was filled in a cylindrical plastic pot (diameter: 10 cm, depth: 10 cm), and the seeds of Japanese millet and oat were sowed and cultivated for 10 days in a greenhouse. The prescribed amount of the emulsifiable concentrates of the test compounds prepared according to Formulation example 2 was diluted with water containing a spreading agent. The volume of the water containing a spreading agent was proportional to 10 liters/are. The resulting herbicide was foliage-applied to the test plants over the top with a small-sized sprayer. After the treatment, the test plants were cultivated for 20 days in a greenhouse to examine the herbicidal activity. Table 4 shows the result.

TABLE 4

| Test compound | Dosage rate of active ingredient (g/a) | Herbicidal activity Japanese millet | Oat |
|---|---|---|---|
| (1) | 40 | 5 | 5 |
| (2) | 40 | 5 | 5 |
| (3) | 40 | 5 | 5 |
| (4) | 40 | 5 | 5 |
| (5) | 40 | 5 | 5 |
| (6) | 40 | 5 | 5 |
| (7) | 40 | 5 | 5 |
| (8) | 40 | 5 | 5 |
| (9) | 40 | 5 | 5 |
| (10) | 40 | 5 | 5 |
| (11) | 40 | 5 | 5 |
| (12) | 40 | 5 | 5 |
| (13) | 40 | 5 | 5 |
| (14) | 40 | 5 | 5 |
| (15) | 40 | 5 | 5 |
| (16) | 40 | 5 | 5 |
| (17) | 40 | 5 | 5 |
| (18) | 40 | 5 | 5 |
| (19) | 40 | 5 | 5 |
| (20) | 40 | 5 | 5 |
| (21) | 40 | 5 | 5 |
| (22) | 40 | 5 | 5 |
| (23) | 40 | 5 | 5 |
| (24) | 40 | 5 | 5 |
| (25) | 40 | 5 | 5 |
| (26) | 40 | 5 | 5 |
| (27) | 40 | 5 | 5 |
| (28) | 40 | 5 | 5 |
| (29) | 40 | 5 | 5 |

TEST EXAMPLE 2

Soil Surface treatment test in plow field

Plow-field soil was filled in a cylindrical plastic pot (diameter: 10 cm, depth: 10 cm), and the seeds of Japanese millet and oat were sowed and covered with the soil. The prescribed amount of the emulsifiable concentrates of the test compounds prepared according to Formulation example 2 was diluted with water. The volume of the water was proportional to 10 liters/are. The resulting herbicide was applied to the soil surface with a small-sized sprayer. After the treatment, the test plants were cultivated for 20 days in a greenhouse to examine the herbicidal activity. Table 5 shows the results.

TABLE 5

| Test compound | Dosage rate of active ingredient (g/a) | Herbicidal activity Japanese millet | Oat |
|---|---|---|---|
| (1) | 40 | 5 | 5 |
| (2) | 40 | 5 | 5 |
| (3) | 40 | 5 | 5 |
| (4) | 40 | 5 | 5 |
| (5) | 40 | 5 | 5 |
| (6) | 40 | 5 | 5 |
| (7) | 40 | 5 | 5 |
| (8) | 40 | 5 | 5 |
| (10) | 40 | 5 | 5 |
| (11) | 40 | 5 | 5 |
| (12) | 40 | 5 | 5 |
| (13) | 40 | 5 | 5 |
| (14) | 40 | 5 | 5 |
| (15) | 40 | 5 | 5 |
| (16) | 40 | 5 | 5 |

TABLE 5-continued

| Test compound | Dosage rate of active ingredient (g/a) | Herbicidal activity Japanese millet | Oat |
|---|---|---|---|
| (17) | 40 | 5 | 5 |
| (18) | 40 | 5 | 5 |

TEST EXAMPLE 3

Foliage treatment test in plow field

Plow-field soil was filled in a cylindrical plastic pot (diameter: 10 cm, depth: 10 cm), and the seeds of Japanese millet, oat, radish and velvetleaf were sowed and cultivated for 10 days in a greenhouse. The prescribed amount of the emulsifiable concentrates of the test compounds prepared according to Formulation example 2 was diluted with water containing a spreading agent. The volume of the water containing a spreading agent was proportional to 10 liters/are. The resulting herbicide was foliage-applied to the test plants over the top with a small-sized sprayer. After the treatment, the test plants were cultivated for 20 days in a greenhouse to examine the herbicidal activity. Table 6 shows the results.

TABLE 6

| Test compound | Dosage rate of active ingredient (g/a) | Herbicidal activity Japanese millet | Oat | Radish | Velvet-leaf |
|---|---|---|---|---|---|
| (1) | 40 | 5 | 5 | 5 | 5 |
| (2) | 40 | 5 | 5 | 5 | — |
| (3) | 40 | 5 | 5 | 5 | 5 |
| (4) | 40 | 5 | 5 | 5 | — |
| (5) | 40 | 5 | 5 | 5 | 5 |
| (7) | 40 | 5 | 5 | 5 | — |
| (8) | 40 | 5 | 5 | 5 | 5 |
| (10) | 40 | 5 | 5 | 5 | — |
| (11) | 40 | 5 | 5 | 5 | — |
| (12) | 40 | 5 | 5 | 5 | 5 |
| (13) | 40 | 5 | 5 | 5 | — |
| (14) | 40 | 5 | 5 | 5 | 5 |
| (15) | 40 | 5 | 5 | 5 | — |
| (16) | 40 | 5 | 5 | 5 | — |

TEST EXAMPLE 4

Treatment test under flooded condition in paddy field

Paddy-field soil was filled in a cylindrical plastic pot (diameter: 8 cm, depth: 12 cm), and the seeds of barnyardgrass were incorporated in 1 or 2 cm depth in the soil. After preparing a paddy field condition by flooding, the test plant was cultivated in a greenhouse. 6 days later (initial stage of emergence of weeds), the prescribed amount of the emulsifiable concentrates of the test compounds prepared according to Formulation example 2 was diluted with 5 ml of water, and applied to the water surface. After the treatment, the test plant was cultivated for 20 days in a greenhouse to examine the herbicidal activity. Table 7 shows the results.

TABLE 7

| Test compound | Dosage rate of active ingredient (g/a) | Herbicidal activity Barnyardgrass |
|---|---|---|
| (1) | 40 | 5 |
| (2) | 40 | 5 |
| (3) | 40 | 5 |
| (4) | 40 | 5 |

TABLE 7-continued

| Test compound | Dosage rate of active ingredient (g/a) | Herbicidal activity Barnyardgrass |
|---|---|---|
| (5) | 40 | 5 |
| (6) | 40 | 5 |
| (7) | 40 | 5 |
| (8) | 40 | 5 |
| (9) | 40 | 5 |
| (10) | 40 | 5 |
| (11) | 40 | 5 |
| (12) | 40 | 5 |
| (13) | 40 | 5 |
| (14) | 40 | 5 |
| (15) | 40 | 5 |
| (16) | 40 | 5 |
| (17) | 40 | 5 |
| (18) | 40 | 5 |
| (19) | 40 | 5 |
| (20) | 40 | 5 |
| (21) | 40 | 5 |
| (22) | 40 | 5 |
| (23) | 40 | 5 |
| (24) | 40 | 5 |
| (25) | 40 | 5 |
| (26) | 40 | 5 |
| (27) | 40 | 5 |
| (28) | 40 | 5 |
| (29) | 40 | 5 |

TEST EXAMPLE 5

Soil treatment test in plow field

Plow-field soil was filled in a vat (area: 33×23 cm$^2$, depth: 11 cm), and the seeds of soybean, cotton, barnyardgrass, johnsongrass and green foxtail were sowed and covered with the soil in 1 or 2 cm depth. The prescribed amount of the emulsifiable concentrates of the test compounds prepared according to Formulation example 2 was diluted with water. The volume of the water was proportional to 10 liters/are. The resulting herbicide was applied to the soil surface with a small-sized sprayer. After the treatment, the test plants were cultivated for 20 days in a greenhouse to examine the herbicidal activity. Table 8 shows the results.

TABLE 8

| Test compound | Dosage rate of active ingredient (g/a) | Herbicidal activity Soybean | Cotton | Barnyardgrass | Johnsongrass | Green foxtail |
|---|---|---|---|---|---|---|
| (1) | 2.5 | 0 | 0 | 5 | 5 | 5 |
| | 0.63 | | | | | |
| (7) | 2.5 | 0 | 0 | 4 | 4 | — |
| (8) | 2.5 | 0 | 0 | 4 | 5 | — |
| (13) | 2.5 | 0 | 0 | 5 | 5 | — |
| A | 2.5 | 0 | 0 | 0 | 1 | 0 |
| B | 2.5 | 0 | 0 | 2 | 1 | 2 |

TEST EXAMPLE 6

Soil treatment test in plow field

Plow-field soil was filled in a vat (area: 33×23 cm$^2$, depth: 11 cm), and the seeds of corn, barnyardgrass, large crabgrass, johnsongrass, green foxtail, oat and fall panicum were sowed and covered with the soil in 1 or 2 cm depth. The prescribed amount of the emulsifiable concentrates of the test compounds prepared according to Formulation example 2 was diluted with water. The volume of the water was proportional to 10 liters/are. The resulting herbicide was applied to the soil surface with a small-sized sprayer. After the treatment, the test plants were cultivated for 20 days in a greenhouse to examine the herbicidal activity. Table 9 shows the results.

TABLE 9

| Test compound | Dosage rate of active ingredient (g/a) | Herbicidal activity Corn | Barnyardgrass | Large crabgrass | Johnsongrass | Green foxtail | Oat | Fall panicum |
|---|---|---|---|---|---|---|---|---|
| (1) | 2.5 | 0 | 5 | 5 | 5 | 5 | 5 | 5 |
| (7) | 2.5 | 0 | 4 | 5 | 4 | — | 4 | 5 |
| (8) | 2.5 | 0 | 4 | 5 | 5 | — | — | 5 |
| (13) | 2.5 | 0 | 5 | 5 | 5 | — | — | 5 |
| A | 2.5 | 0 | 0 | 1 | 1 | 0 | 0 | 1 |
| C | 2.5 | 0 | 3 | 1 | 1 | 1 | 0 | 5 |

TEST EXAMPLE 7

Soil treatment test in plow field

Plow-field soil was filled in a vat (area: 33×23 cm$^2$, depth: 11 cm), and the seeds of wheat, wild oat, blackgrass and annual bluegrass were sowed and covered with the soil in 1 or 2 cm depth. The prescribed amount of the emulsifiable concentrates of the test compounds prepared according to Formulation example 2 was diluted with water. The volume of the water was proportional to 10 liters/are. The resulting herbicide was applied to the soil surface with a small-sized sprayer. After the treatment, the test plants were cultivated for 30 days in a greenhouse to examine the herbicidal activity. Table 10 shows the results.

TABLE 10

| Test compound | Dosage rate of active ingredient (g/a) | Herbicidal activity Wheat | Wild oat | Blackgrass | Annual bluegrass |
|---|---|---|---|---|---|
| (1) | 2.5 | — | 5 | 5 | 5 |
| | 0.63 | 0 | — | 5 | 4 |
| B | 2.5 | 1 | 0 | 2 | 0 |
| | 0.63 | 0 | 0 | 0 | 0 |

TEST EXAMPLE 8

Foliage treatment test in plow field

Plow-field soil was filled in a vat (area: 33×23 cm$^2$, depth: 11 cm), and the seeds of soybean, cotton, barnyardgrass, large crabgrass, johnsongrass, green foxtail, oat and annual bluegrass were sowed and cultivated for 18 days. The prescribed amount of the emulsifiable concentrates of the test compounds prepared according to Formulation example 2 was diluted with water containing a spreading agent. The volume of the water containing a spreading agent was proportional to 10 liters/are. The resulting herbicide was uniformly applied to the entire foliage of the test plants over the top with a small-sized sprayer. At this time, the growth of the weeds and crops usually varied with the kind thereof. However they arrived at the cotyledonous stage through 3-leaf stage and had a height of from 7 to 15 cm. Twenty days after the treatment, the herbicidal activity was examined. Table 11 shows the results. These tests were carried out in a greenhouse through the entire period of test.

TABLE 11

| Test compound | Dosage rate of active ingredient (g/a) | Herbicidal activity | | | | | | | |
|---|---|---|---|---|---|---|---|---|---|
| | | Soybean | Cotton | Barnyard-grass | Large crab-grass | Johnson-grass | Green fox-tail | Oat | Annual blue-grass |
| (1) | 2.5 | — | 0 | 5 | 5 | 5 | 5 | 5 | 4 |
| | 0.63 | — | 0 | 5 | 4 | 5 | 5 | 5 | 4 |
| (3) | 2.5 | — | 0 | 5 | 5 | 5 | 4 | 5 | — |
| (4) | 2.5 | — | 1 | 5 | 5 | 5 | 5 | 5 | 4 |
| | 0.63 | 0 | 0 | 4 | 4 | 5 | — | 4 | — |
| (5) | 2.5 | — | 0 | 5 | 5 | 5 | 5 | 5 | 4 |
| | 0.63 | 0 | 0 | 4 | 5 | 5 | 4 | 4 | — |
| (8) | 2.5 | — | 0 | 5 | 5 | 5 | 4 | 5 | 4 |
| | 0.63 | 1 | 0 | 4 | 5 | 5 | 4 | 5 | — |
| (11) | 2.5 | — | 0 | 5 | 5 | 5 | 4 | 5 | 4 |
| | 0.63 | 0 | 0 | 4 | — | 5 | 4 | 5 | — |
| (12) | 2.5 | — | 0 | 5 | 4 | 5 | 5 | 5 | 4 |
| | 0.63 | 1 | 0 | 4 | — | 5 | — | 4 | 4 |
| (13) | 2.5 | — | 0 | 5 | 5 | 5 | 5 | 5 | — |
| | 0.63 | 0 | 0 | 4 | — | 5 | 4 | 4 | — |
| (17) | 2.5 | — | 0 | 5 | 4 | 5 | 4 | 5 | — |
| (18) | 2.5 | — | 0 | 5 | 4 | 5 | 5 | 5 | 4 |
| A | 2.5 | 0 | 0 | 3 | 1 | 2 | 3 | 3 | 2 |
| | 0.63 | 0 | 0 | 1 | 0 | 0 | 1 | 0 | 0 |
| B | 2.5 | 0 | 0 | 3 | 1 | 2 | 3 | 3 | 3 |
| | 0.63 | 0 | 0 | 2 | 0 | 0 | 2 | 0 | 0 |

TEST EXAMPLE 9

Foliage treatment test in plow field

Plow-field soil was filled in a vat (area: $33\times23$ cm$^2$, depth: 11 cm), and the seeds of corn, larger crabgrass, johnsongrass, green foxtail and oat were sowed and cultivated for 18 days. The prescribed amount of the emulsifiable concentrates of the test compounds prepared according to Formulation example 2 was diluted with water. The volume of the water was proportional to 10 liters/are. The resulting herbicide was uniformly applied to the entire foliage of the test plants over the top with a small-sized sprayer. At this time, the growth of the weeds and crops usually varied with the kind thereof. However they arrived at the 1-leaf stage through 2-leaf stage and had a height of from 7 to 15 cm. Twenty days after the treatment, the herbicidal activity was examined. Table 12 shows the results. These tests were carried out in a greenhouse through the entire period of test.

TABLE 12

| Test compound | Dosage rate of active ingredient (g/a) | Herbicidal activity | | | | |
|---|---|---|---|---|---|---|
| | | Corn | Large crab-grass | John-son-grass | Green fox-tail | Oat |
| (1) | 0.63 | 0 | 4 | 5 | 5 | 4 |
| | 0.16 | 0 | — | 4 | — | 4 |
| (4) | 0.63 | 0 | 4 | 5 | — | 4 |
| (5) | 0.63 | 1 | 5 | 5 | 4 | 4 |
| (8) | 0.63 | 1 | 5 | 5 | 4 | 5 |
| (11) | 0.63 | 0 | — | 5 | 4 | 5 |
| (14) | 0.63 | 1 | — | 5 | 4 | 5 |
| C | 0.63 | 3 | 2 | 1 | 4 | 3 |

TEST EXAMPLE 10

Treatment test under flooded condition in paddy field

Paddy-field soil was filled in 1/5000 area Wagner's pots, and the seeds of barnyardgrass were incorporated in 1 to 2 cm depth in the soil. After preparing a paddy field condition by flooding, rice seedlings in a 3-leaf stage were transplanted and cultivated in a greenhouse. 4 days later, the prescribed amount of the emulsifiable concentrates of the test compounds prepared according to Formulation example 2 was diluted with 10 ml of water and applied to the water surface, and the depth of water was made 4 cm. After the treatment, the test plants were cultivated for 20 days in a greenhouse to examine the herbicidal activity. Table 13 shows the results. In this test, water was leaked in a volume corresponding to a water level of 3 cm/day for 2 days from the day subsequent to the treatment.

TABLE 13

| Test compound | Dosage rate of active ingredient (%) | Herbicidal activity | |
|---|---|---|---|
| | | Rice | Barnyardgrass |
| (3) | 0.32 | 0 | 5 |
| (4) | 0.32 | 0 | 5 |
| E | 0.32 | 0 | 0 |

TEST EXAMPLE 11

Foliage treatment test in plow field

Plow field was ridged so that the upper row had 1 meter width. The seeds of corn, large crabgrass, johnsongrass, giant foxtail and barnyardgrass were sowed there. When the corn grew to the 4-leaf stage and the other weeds grew to the 1-leaf stage through 4-leaf stage, the rows were partitioned into test plots of 3 m$^2$ in area. The prescribed amount of the emulsifiable concentrates of the test compounds prepared according to Formulation example 2 was diluted with water. The volume of the water was proportional to 3 liters/are. The resulting herbicide was foliage-applied to the whole surface of the test plots with a small-sized sprayer. The procedure was repeated three times. 23 days later, the herbicidal activity was examined. Table 14 shows the results.

TABLE 14

| Test compound | Dosage rate of active ingredient (g/a) | Herbicidal activity | | | | |
|---|---|---|---|---|---|---|
| | | Corn | Large crab-grass | John-son-grass | Giant fox tail | Barn-yard-grass |
| (1) | 1 | 0 | 5 | 4 | 5 | 5 |
| D | 20 | 0 | 3 | 0 | 3 | 3 |

The present compounds have a high herbicidal activity against various problematic weeds in soil treatment and foliage treatment in plow field as well as in treatment under flooded condition in paddy field, and besides they exhibit a high selectivity to the weeds from the main crops, so that they can be used in various applications as active ingredient for herbicides.

What is claimed is:

1. A cyclohexenone derivative represented by the formula,

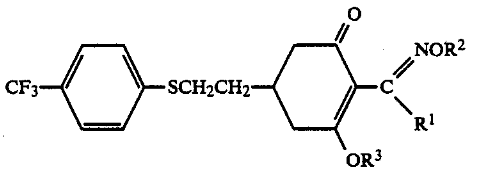

wherein $R^1$ represents a $(C_1-C_3)$alkyl group, $R^2$ represents a $(C_1-C_3)$alkyl, $(C_3-C_4)$alkenyl, propargyl or chloroallyl group, and $R^3$ represents a $(C_1-C_{12})$alkyl, $(C_3-C_5)$alkenyl, propargyl, halo$(C_2-C_3)$alkyl, halo$(C_3-C_4)$alkenyl, $(C_3-C_6)$cycloalkyl, $(C_5-C_7)$cycloalkenyl, $(C_1-C_8)$alkoxy$(C_1-C_2)$alkyl, methylthiomethyl, halo$(C_2-C_4)$alkoxymethyl, benzyloxymethyl (which may be substituted with a $(C_1-C_2)$alkyl group or halogen atom), carboxy$(C_1-C_4)$alkyl, $(C_1-C_5)$alkoxycarbonyl$(C_1-C_4)$alkyl, di$(C_1-C_3)$alkylcarbamoyl, di$(C_1-C_3)$alkylthiocarbamoyl, O,O-di$(C_1-C_3)$alkoxyphosphinyl, $(C_1-C_{11})$alkylcarbonyl, $(C_2-C_4)$alkenylcarbonyl, $(C_3-C_6)$cycloalkylcarbonyl, $(C_3-C_6)$cycloalkylacetyl, chrysanthemoyl, benzoyl (which may be substituted with a $(C_1-C_2)$alkyl group or halogen atom), naphthalenecarbonyl, pyridinecarbonyl, furoyl or thenoyl (which may be substituted with a $(C_1-C_2)$alkyl group or halogen atom).

2. The cyclohexenone derivative according to claim 1, wherein $R^1$ is methyl and $R^2$ is ethyl.

3. The cyclohexenone derivative according to claim 2, wherein $R^3$ is methyl, propargyl, $(C_1-C_5)$alkoxymethyl, halo$(C_2-C_4)$alkoxymethyl, methylthiomethyl, carboxymethyl, 1-carboxyethyl, $(C_1-C_{11})$alkylcarbonyl, thenoyl.

4. The compound according to claim 3, of the formula,

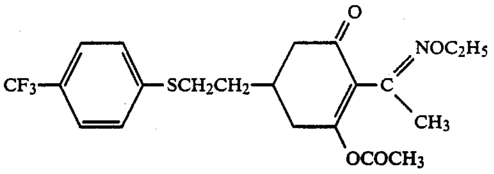

5. The compound according to claim 3, of the formula,

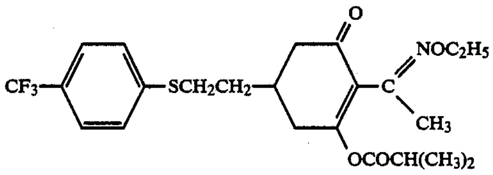

6. The compound according to claim 3, of the formula,

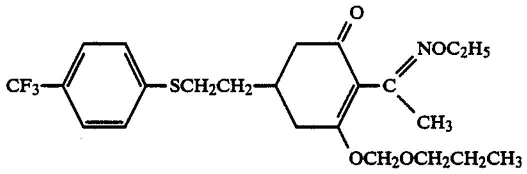

7. The compound according to claim 3, of the formula,

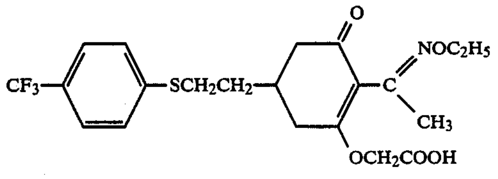

8. A herbicidal composition which comprises as an active ingredient a herbicidally effective amount of the compound according to claim 1 and a carrier.

9. A method for controlling undesired weeds, which comprises applying a herbicidally effective amount of the compound according to claim 1 and a carrier to the area where undesired weeds grow or will grow.

10. The method according to claim 7, wherein the area is a corn field.

11. Use of the compound according to claim 1 as a herbicide.

* * * * *